United States Patent
Bahrami

(10) Patent No.: US 12,268,488 B2
(45) Date of Patent: Apr. 8, 2025

(54) NONINVASIVE VITAL SIGNS MEASUREMENT SYSTEM

(71) Applicant: Bionous, LLC, Camano Island, WA (US)

(72) Inventor: Ali Bahrami, Camano Island, WA (US)

(73) Assignee: Bionous, LLC, Camano Island, WA (US)

( * ) Notice: Subject to any disclaimer, the term of this patent is extended or adjusted under 35 U.S.C. 154(b) by 681 days.

(21) Appl. No.: 17/418,492

(22) PCT Filed: Dec. 27, 2019

(86) PCT No.: PCT/US2019/068701
§ 371 (c)(1),
(2) Date: Jun. 25, 2021

(87) PCT Pub. No.: WO2020/140013
PCT Pub. Date: Jul. 2, 2020

(65) Prior Publication Data
US 2022/0079460 A1     Mar. 17, 2022

Related U.S. Application Data

(60) Provisional application No. 62/785,746, filed on Dec. 28, 2018.

(51) Int. Cl.
*A61B 5/024*     (2006.01)
*A61B 5/00*      (2006.01)
(Continued)

(52) U.S. Cl.
CPC ........ *A61B 5/02427* (2013.01); *A61B 5/0205* (2013.01); *A61B 5/02405* (2013.01);
(Continued)

(58) Field of Classification Search
None
See application file for complete search history.

(56) References Cited

U.S. PATENT DOCUMENTS

| | | | |
|---|---|---|---|
| 7,377,794 B2 * | 5/2008 | Al-Ali | A61B 5/1495 600/344 |
| 2010/0100392 A1 * | 4/2010 | Rothman | G16H 50/20 705/2 |

(Continued)

FOREIGN PATENT DOCUMENTS

WO    WO 2020/140009 A1    7/2020

OTHER PUBLICATIONS

Nonin—youtube video: https://www.youtube.com/watch?v=QRdNG3YN3tE Nonin 8000Q2 Ear Clip Pulse Oximeter Sensor: Use Sep. 13, 2013 (Year: 2013).*

(Continued)

*Primary Examiner* — Jay B Shah
(74) *Attorney, Agent, or Firm* — Wolf, Greenfield & Sacks, P.C.

(57) ABSTRACT

Methods and apparatus for noninvasive measurement of vital signs is provided. The apparatus comprises at least one sensor configured to sense biological signals including a photoplethysmogram (PPG), and at least one computer processor programmed to determine a plurality of vital signs based, at least in part, on the sensed biological signals, wherein the plurality of vital signs include at least two of heart rate, blood oxygenation, heart rate variability, blood pressure, blood sugar, cholesterol, pulse rate, pulse pressure, temperature, and respiration rate.

15 Claims, 10 Drawing Sheets

(51) Int. Cl.
    *A61B 5/0205*     (2006.01)
    *A61B 5/08*     (2006.01)
    *A61B 5/1455*     (2006.01)

(52) U.S. Cl.
    CPC ........ *A61B 5/02438* (2013.01); *A61B 5/0816* (2013.01); *A61B 5/14552* (2013.01); *A61B 5/6816* (2013.01); *A61B 5/683* (2013.01); *A61B 5/742* (2013.01); *A61B 2503/40* (2013.01)

(56) References Cited

U.S. PATENT DOCUMENTS

| | | | |
|---|---|---|---|
| 2013/0253334 A1* | 9/2013 | Al-Ali | A61B 5/7405 600/300 |
| 2014/0114199 A1* | 4/2014 | Lamego | A61B 5/6826 600/479 |
| 2017/0127959 A1* | 5/2017 | Paulussen | A01K 29/005 |
| 2017/0156676 A1 | 6/2017 | Ferber et al. | |
| 2017/0185284 A1 | 6/2017 | Bhavaraju et al. | |
| 2017/0308671 A1 | 10/2017 | Bahrami et al. | |

OTHER PUBLICATIONS

Nonin 8000Q2 SpO2 Ear Clip Sensor Quick Guide; P/N 9477-101-01; 2013 https://www.nonin.com/wp-content/uploads/2018/09/8000Q2-Quick-Start-Guide.pdf (Year: 2013).*

International Search Report and Written Opinion mailed Apr. 1, 2020 in connection with International Application No. PCT/US2019/068701.

International Preliminary Report on Patentability mailed Jul. 8, 2021 in connection with International Application No. PCT/US2019/068701.

\* cited by examiner

NONINVASIVE VITAL SIGNS MEASUREMENT SYSTEM

CROSS-REFERENCE TO RELATED APPLICATIONS

This Application is a national stage filing under 35 U.S.C. 371 of International Patent Application Serial No. PCT/US2019/068701, filed Dec. 27, 2019, entitled "NONINVASIVE VITAL SIGNS MEASUREMENT SYSTEM," which claims priority under 35 U.S.C. 119 (e) to U.S. Provisional Application Ser. No. 62/785,746, filed Dec. 28, 2018, entitled "NONINVASIVE VITAL SIGNS MEASUREMENT SYSTEM," the entire contents of each of which is incorporated herein by reference in its entirety.

BACKGROUND

Photoplethysmography (PPG) is a noninvasive diagnostic technique for estimating changes in blood volume in the microvascular bed of tissue (e.g., skin tissue). In PPG, tissue is illuminated with light and the reflected light is measured. A photoplethysmogram may be obtained using a pulse oximeter, which illuminates the skin and measures changes in light absorption to determine oxygen saturation and heart rate.

SUMMARY

Some embodiments relate to an apparatus for noninvasive measurement of vital signs. The apparatus comprising at least one sensor configured to sense biological signals including a photoplethysmogram (PPG), and at least one computer processor programmed to determine a plurality of vital signs based, at least in part, on the sensed biological signals, wherein the plurality of vital signs include at least two of heart rate, blood oxygenation, heart rate variability, blood pressure, blood sugar, cholesterol, pulse rate, pulse pressure, temperature, and respiration rate.

In one aspect, the apparatus further comprises a display configured to display a user interface with which a user may interact while the biological signals are sensed.

In another aspect, the display comprises a touch screen display with which the use may interact using touch.

In another aspect, the apparatus includes a casing, wherein a first side of the casing is substantially flat and a second side of the casing includes a recessed portion.

In another aspect, the recessed portion includes the at least one sensor.

In another aspect, the first side of the casing is approximately one inch by one inch.

In another aspect, the apparatus further comprises a communications interface configured to communicate with a computer, a smartphone, and/or a tablet.

In another aspect, the apparatus comprises a first portion that includes the at least one sensor and a second portion that is reversibly removable from the first portion.

In another aspect, the apparatus further comprises at least one fastener configured to couple the first portion and the second portion.

In another aspect, the at least one fastener includes at least one magnet arranged on the first portion and/or the second portion.

In another aspect, the at least one fastener is configured to secure the apparatus to a body part of an animal.

In another aspect, the body part is an ear of the animal.

In another aspect, the at least one computer processor is further programmed to determine a score based, at least in part, on the determined plurality of vital signs.

In another aspect, the apparatus further comprises a communication interface configured to wirelessly communicate information about the measured biological signals and/or the determined plurality of vital signs to a computing device.

In another aspect, the apparatus further comprises at least one light source configured to illuminate a body part of a user with light, and wherein the at least one sensor is configured to sense light reflected from the body part of the user to determine the PPG.

In another aspect, the apparatus is wearable by a user.

In another aspect, the user is a non-human animal.

Some embodiments relate to a method of noninvasively assessing wellness of an animal. The method comprises sensing one or more biological signals from a body part of a user using at least one sensor, wherein the one or more biological signals include a photoplethysmogram (PPG), and determining, using at least one computer processor, a plurality of vital signs for the animal based, at least in part, on the sensed one or more biological signals, wherein the plurality of vital signs include at least two of heart rate, blood oxygenation, heart rate variability, blood pressure, blood sugar, cholesterol, pulse rate, pulse pressure, temperature, and respiration rate.

In one aspect, the method further comprises displaying on a user interface, at least some of the determined plurality of vital signs.

In another aspect, the method further comprises communicating information about the sensed one or more biological signals and/or the plurality of vital signs to a computer, a smartphone, and/or a tablet.

In another aspect, the method further comprises arranging the body part of the animal in proximity to the at least one sensor such that the at least one sensor is secured to the body part of the animal.

In another aspect, the body part of the animal is an ear of the animal, and wherein the at least one sensor is secured to the ear.

In another aspect, the method further comprises determining a score based, at least in part, on the determined plurality of vital signs.

In another aspect, the method further comprises illuminating the body part of a user with light output from at least one light source, and sensing, by the at least one sensor, light reflected from the body part of the user to determine the PPG.

Some embodiments relate to at least one non-transitory computer readable medium having encoded thereon, a plurality of instructions that, when executed by at least one computer processor, perform a method of noninvasively assessing wellness of an animal, The method comprises sensing one or more biological signals from a body part of a user using at least one sensor, wherein the one or more biological signals include a photoplethysmogram (PPG), and determining, using at least one computer processor, a plurality of vital signs for the animal based, at least in part, on the sensed one or more biological signals, wherein the plurality of vital signs include at least two of heart rate, blood oxygenation, heart rate variability, blood pressure, blood sugar, cholesterol, pulse rate, pulse pressure, temperature, and respiration rate.

In one aspect, the method further comprises displaying on a user interface, at least some of the determined plurality of vital signs.

In another aspect, the method further comprises communicating information about the sensed one or more biological signals and/or the plurality of vital signs to a computer, a smartphone, and/or a tablet.

In another aspect, the method further comprises arranging the body part of the animal in proximity to the at least one sensor such that the at least one sensor is secured to the body part of the animal.

In another aspect, the body part of the animal is an ear of the animal, and wherein the at least one sensor is secured to the ear.

In another aspect, the method further comprises determining a score based, at least in part, on the determined plurality of vital signs.

In another aspect, the method further comprises illuminating the body part of a user with light output from at least one light source, and sensing, by the at least one sensor, light reflected from the body part of the user to determine the PPG.

Some embodiments relate to an apparatus for noninvasive measurement of vital signs, said apparatus comprising: sensors for capturing biological signals including a photoplethysmogram (PPG); and at least one computer processor programmed to determine vital signs based, at least in part, on the captured biological signals, wherein the vital signs include blood pressure, blood sugar, blood cholesterol, pulse, pulse pressure, temperature, and respiration rate.

In one aspect, the apparatus further comprises a touch screen display configured to display a user interface with which a user may interact while the biological signals are captured.

In another aspect, the apparatus is configured for use in multiple positions.

In another aspect, the apparatus includes a casing, wherein a first side of the casing is flat and a second side of the casing is not flat and includes the sensors.

In another aspect, the first side of the casing is approximately one inch by one inch.

In another aspect, the apparatus further comprises a communications interface configured to communicate with a computer, a smartphone, and/or a tablet.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

A conventional pulse oximeter used to perform PPG measurement monitors the perfusion of blood to the dermis and subcutaneous tissue of the skin. With each cardiac cycle, the heart pumps blood to the periphery. Even though this pressure pulse may be damped by the time it reaches the skin, the pressure pulse is strong enough to distend the arteries and arterioles in the subcutaneous tissue. If the pulse oximeter is attached without compressing the skin, a pressure pulse can also be observed from the venous plexus, as a small secondary peak in the signal.

Figure 1:
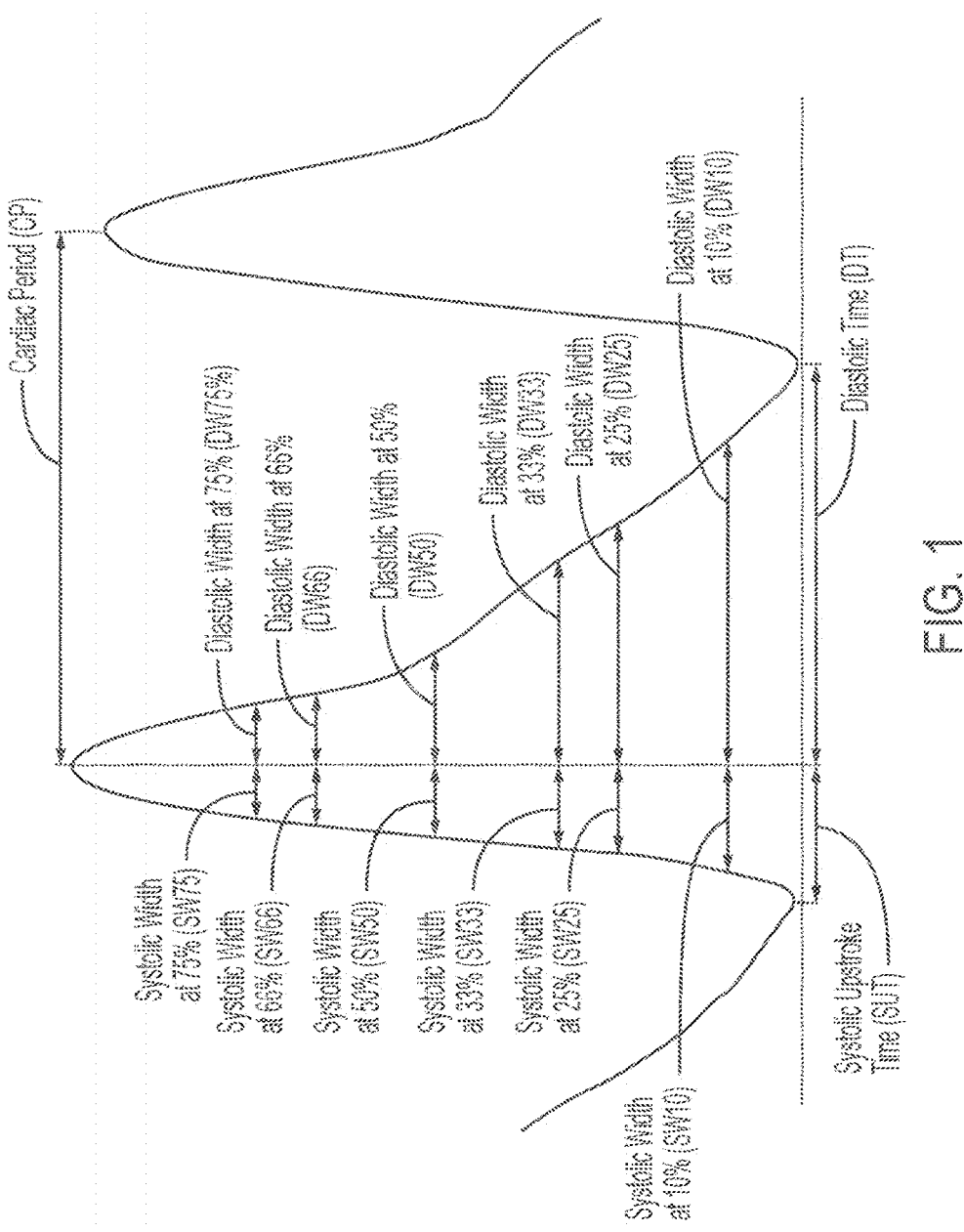
FIG. 1 is a plot of a photoplethysmogram (PPG) signal recorded using a single LED PPG system.

The change in volume caused by the pressure pulse is detected by illuminating the skin with light from a light source (e.g., a light-emitting diode (LED)), and measuring the amount of light either transmitted or reflected to a photosensitive device (e.g., a photodiode). Each cardiac cycle appears as a peak in the signal output from the photodiode, as shown in FIG. 1. Because blood flow to the skin may be modulated by multiple other physiological systems, the PPG may also be used to, in addition to cardiac monitoring, monitor breathing, hypovolemia, and other circulatory conditions. Additionally, the shape of the PPG waveform differs from subject to subject, and varies with the location and manner in which the pulse oximeter is attached.

Figure 2:
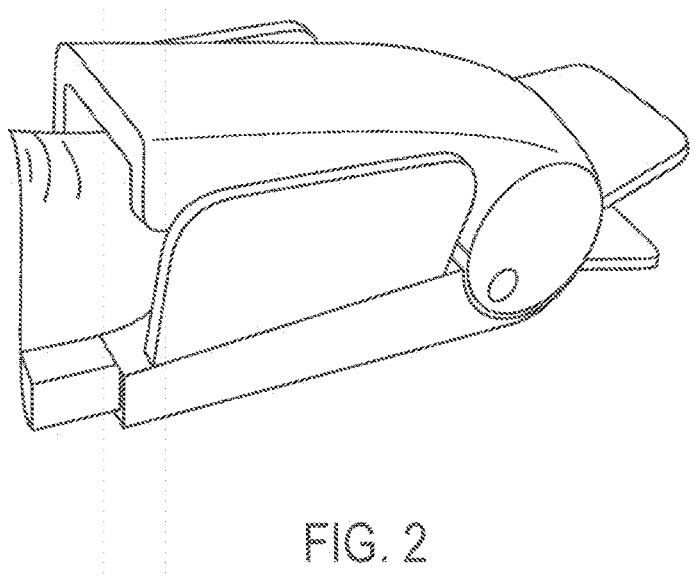
FIG. 2 illustrates a transmission-based PPG system.

A typical optical system for peripheral capillary oxygen saturation ($SpO_2$) measurement includes light emitting diodes (LEDs) that illuminate tissue and a photodiode that receives the transmitted or reflected light. Two types of optical arrangements for performing $SpO_2$ measurements are transmissive and reflective. For transmissive arrangements, the photodiode and the LED are placed on opposite sides of a human body part (e.g., a finger), with the photodiode collecting the residual light after absorption from the various components of the body part. For reflective arrangements, the photodiode and the LED are placed on the same side of the illuminated body part and the photodiode collects the light reflected from various depths underneath the skin. Finger-clip type probes commonly used in a medical clinic, an example of which is shown in FIG. 2, are typical of the transmissive type. Such finger-clip type probes typically include a cable that couples to a computing device and a display to display $SpO_2$ measurements.

The inventor has recognized and appreciated that existing devices for capturing PPG information may be improved. Some embodiments are directed to small noninvasive vital signs measurement systems that can be used to periodically and/or continuously monitor vital signs for a human or other animal. As discussed in more detail, vital signs that can be measured using various embodiments of the systems described herein include, but are not limited to, blood pressure, blood sugar, blood cholesterol, pulse rate, pulse pressure, body temperature, and respiration rate.

Figure 3C:
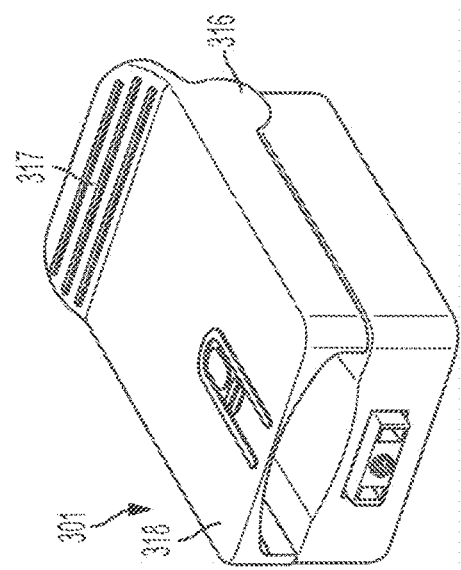
FIG. 3C illustrates a finger clip version of the noninvasive vital signs measurement system of FIG. 3A.
Figure 3B:
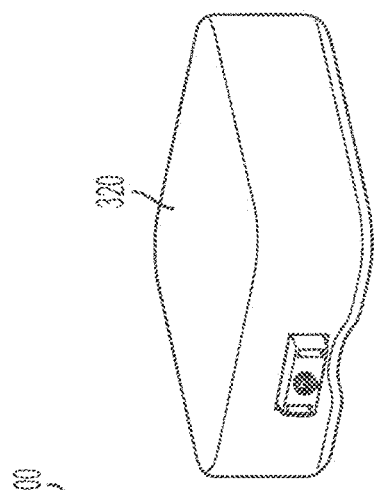
FIGS. 3A and 3B illustrate, respectively, a top view and a bottom view of noninvasive vital signs measurement device in accordance with some embodiments.
Figure 3A:
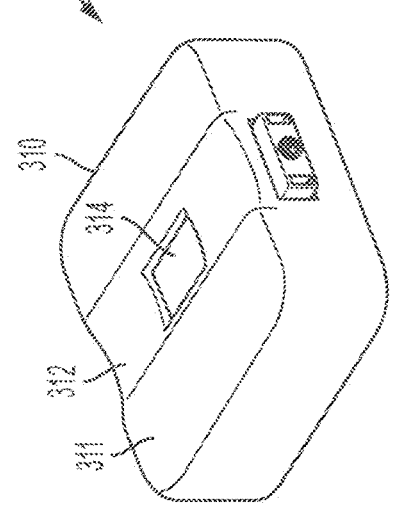

FIGS. 3A and 3B show different views of a first embodiment of a noninvasive vital signs measurement system 300. FIG. 3C shows a second embodiment of a noninvasive vital signs measurement system 301. The measurement systems 300 and 301 shown in FIGS. 3A, 3B, and 3C are also referred to herein as the Phware® Sense. Though shown as a square or rectangular device, it should be appreciated that not all embodiments of the noninvasive vital signs measurement system are limited to being square-shaped or rectangular-shaped. As shown, system 300 includes a casing having a first surface 310 and a second surface 320 arranged opposite the first surface. Second surface 320 is configured to be substantially flat so that system 300 can be placed on a substantially flat surface when the system is used. The first surface 310 includes flat portions 311 and a recessed portion 312 within which a user can place a body part (e.g., a finger) to use the system 300. Within the recessed portion 312 is a sensor 314 over which the user's finger is placed to make a vital signs measurement, as discussed in further detail below. As shown, system 301 is a finger clip version of a noninvasive vital signs measurement system similar to system 300. In addition to the aforementioned components of system 300, system 301 also includes a top portion 318 configured to be opened using magnetic rotating hinge 316 and tab 317.

The design of the systems 300 and 310 enable users to place the flat side of the system (i.e., second surface 320) on any surface and to place the tip of a finger (e.g., the index finger) on the other (non-flat) side (i.e., first surface 310) of the device for capturing biological signals including a photoplethysmogram (PPG). PPG is an optically-obtained plethysmogram, a volumetric measurement of an organ. The unique design of the system 300 allows for an easy and comfortable way to measure vital signs such as blood pressure or blood sugar without requiring the use of a cuff/pump or finger pricking. In some embodiments, the systems 300 and 301 are portable such that the system may fit within a jacket or pants pocket or handbag. In some embodiments, the size of system 300 is approximately the size of a quarter (e.g., about 1 inch by 1 inch) or smaller.

Figure 4A:
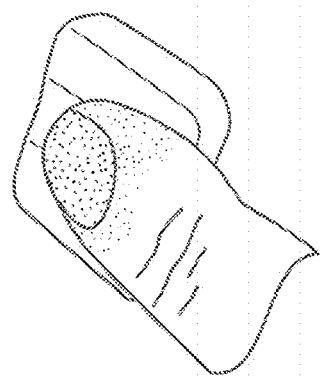
FIG. 4A illustrates the noninvasive vital signs measurement device of FIG. 3A when in use.
Figure 5:
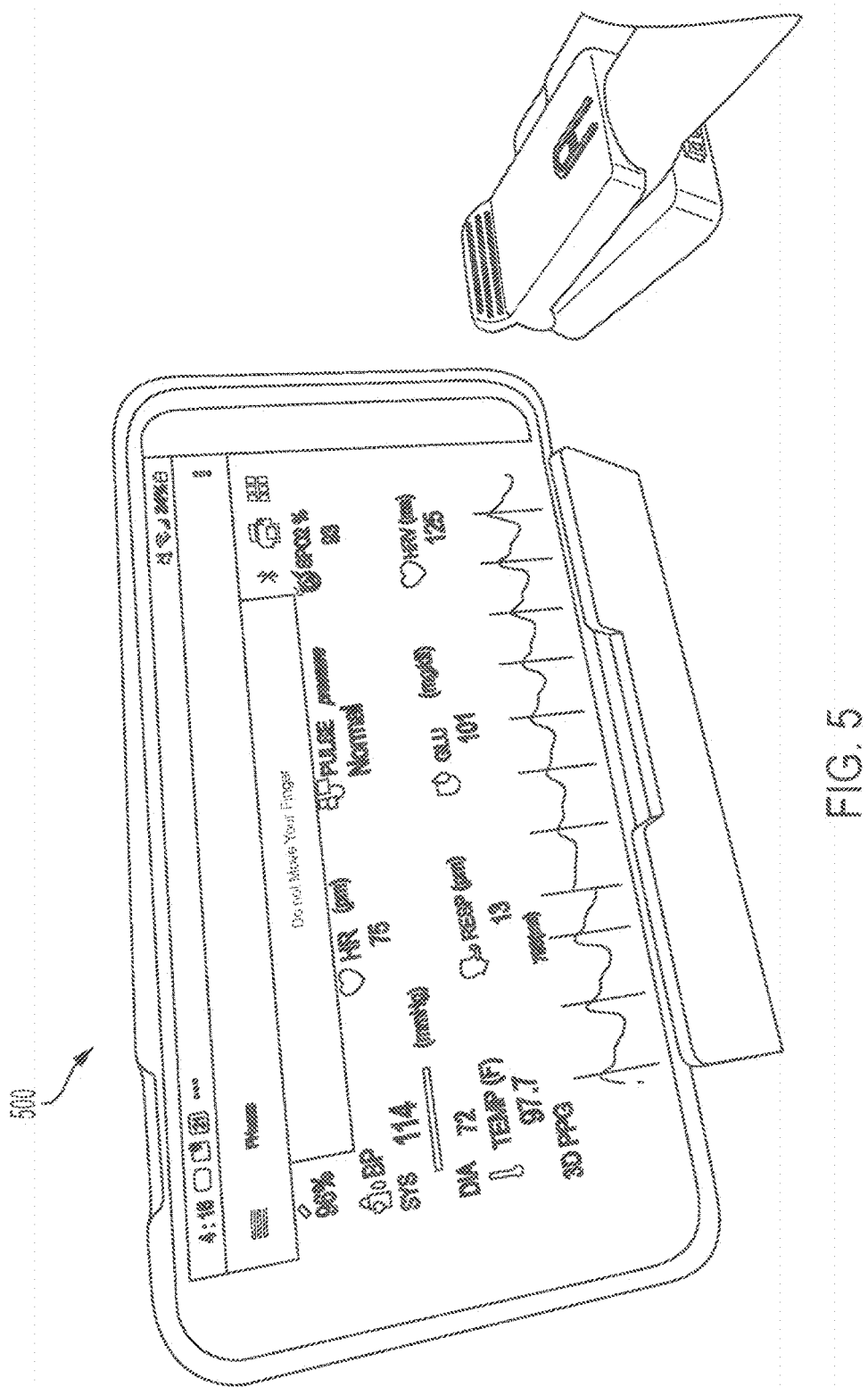
FIG. 5 illustrates a display configured to display vital signs measured using a noninvasive vital signs measurement device in accordance with some embodiments.

FIG. 4A illustrates an example of the system 300, and FIG. 5 illustrates an example of system 301 in use. As shown, a finger placed on the sensor 314 is illuminated with light emitted from the device and changes in light absorption by the tissue in the finger are measured. The reflected light from the skin is sensed by the sensor 314 and processed (e.g., using one or more machine learning algorithms) to determine vital signs including, but not limited to, blood sugar and cholesterol.

Figure 4B:
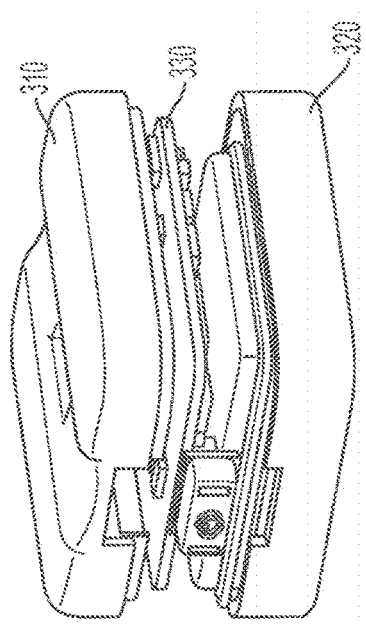
FIG. 4B illustrates an exploded view of the noninvasive vital signs measurement device of FIG. 3A.

FIG. 4B shows an exploded view of system 300. As shown, system 300 includes circuitry 330 having integrated thereon one or more light sources (e.g., one or more light emitting diodes (LEDs)) and sensor(s) 314 used to detect light reflected from the user's finger when placed in the recessed portion 312 of the first surface 310. System 300 also includes communication circuitry to communicate data to a device with a display (e.g., a smartphone, tablet, laptop computer, or other computing device) for displaying results of vital signs measurements sensed by sensor 314 of system 300. Communication circuitry may include, for example, wireless transmission circuitry (e.g., near field communication (NFC), radio frequency (RF), Bluetooth, etc.) to transfer the data for further processing and/or display. In some embodiments, circuitry 330 also includes at least one computer processor programmed to process the output of sensor(s) 314 to prior to transmission of the data for further processing and/or display.

Some embodiments are related to an innovative design for measuring vital signs and blood characteristics for deployment on a host device, such as a computer, smart phone, or tablet, having at least one processor (e.g., a central processing unit (CPU)) and a display.

FIG. 5 illustrates an example of a display 500 configured to communicate with a noninvasive vital signs measurement system (e.g., system 300) and to display measured vital signs. For instance, display 500 may be included as part of a portable computing device (e.g., a smartphone). As shown, display 500 is configured to display a PPG waveform and one or more vital signs measurements determined based, at least in part, on the PPG measurements. For instance, display 500 may be configured to display blood pressure, pulse rate, oxygen saturation ($SpO_2$), body temperature, a glucose measurement, a cholesterol measurement, and a respiration rate. It should be appreciated however, that not all embodiments require the display of multiple types of vital signs including, but not limited to the vital signs shown on the display of FIG. 5. For instance, some embodiments may only display a single vital signs measurement or no vital signs measurements at all. Rather, some embodiments may be configured to compare one or more measured vital signs to a threshold value or range and provide an indication when the vital signs measurement deviates from the threshold value and/or is outside of the range. Such an indication may alert a user of the measurement system or another user (e.g., a pet's owner) of the deviation. The provided indication may be a visual indication (e.g., as shown in FIG. 5), an audio indication, a tactile indication, or any combination thereof, as embodiments are not limited in this respect.

Figure 6A:
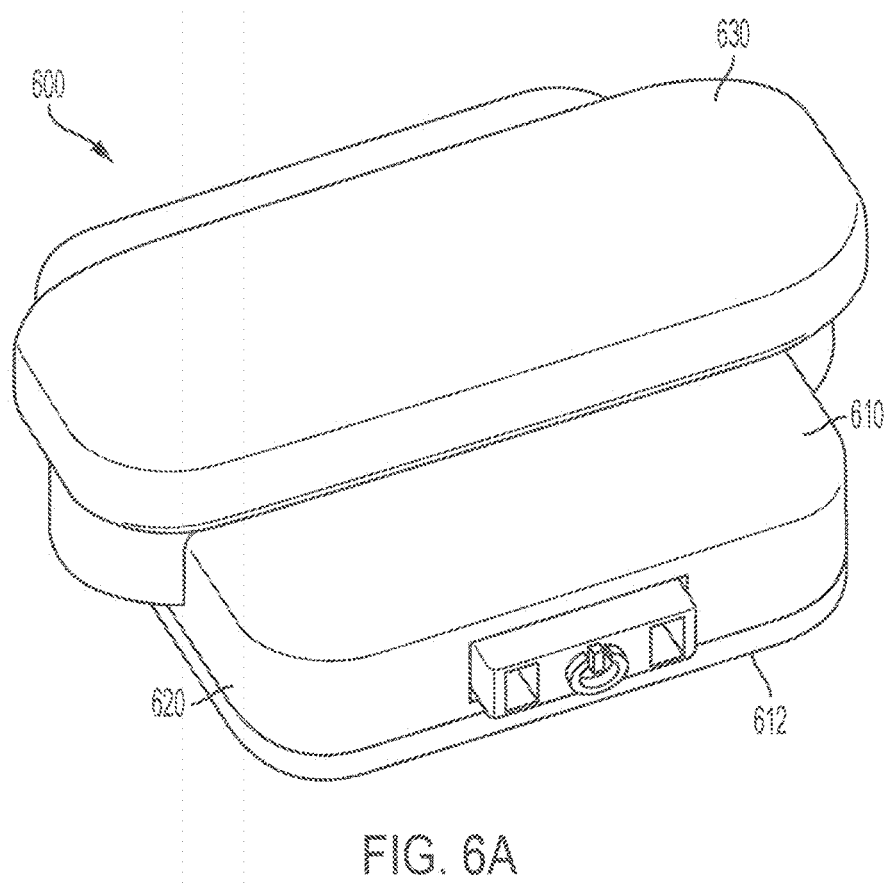
FIGS. 6A and 6B illustrate, respectively, a closed arrangement and an open arrangement of a noninvasive vital signs measurement device in accordance with some embodiments.

FIG. 6A shows an example of an alternative noninvasive vital signs measurement system 600 in accordance with some embodiments. System 600 includes some similarities to systems 300 and 301 described in connection with FIG. 3A and FIG. 3C, respectively. For instance, system 600 includes a casing having a first surface 610 and a second surface 612 arranged opposite the first surface. Unlike systems 300 and 301, system 600 is designed to be worn in contact with a body part (e.g., an ear) rather than being placed on a surface such as a table. Accordingly, although shown as flat surfaces, neither first surface 610 nor second surface 620 need include flat portions. For instance, in some embodiments one or both of first surface 610 and second surface 620 may be contoured and/or flexible to facilitate the positioning of the system 600 in contact with a user's body part from which vital signs measurements will be made.

Figure 6B:
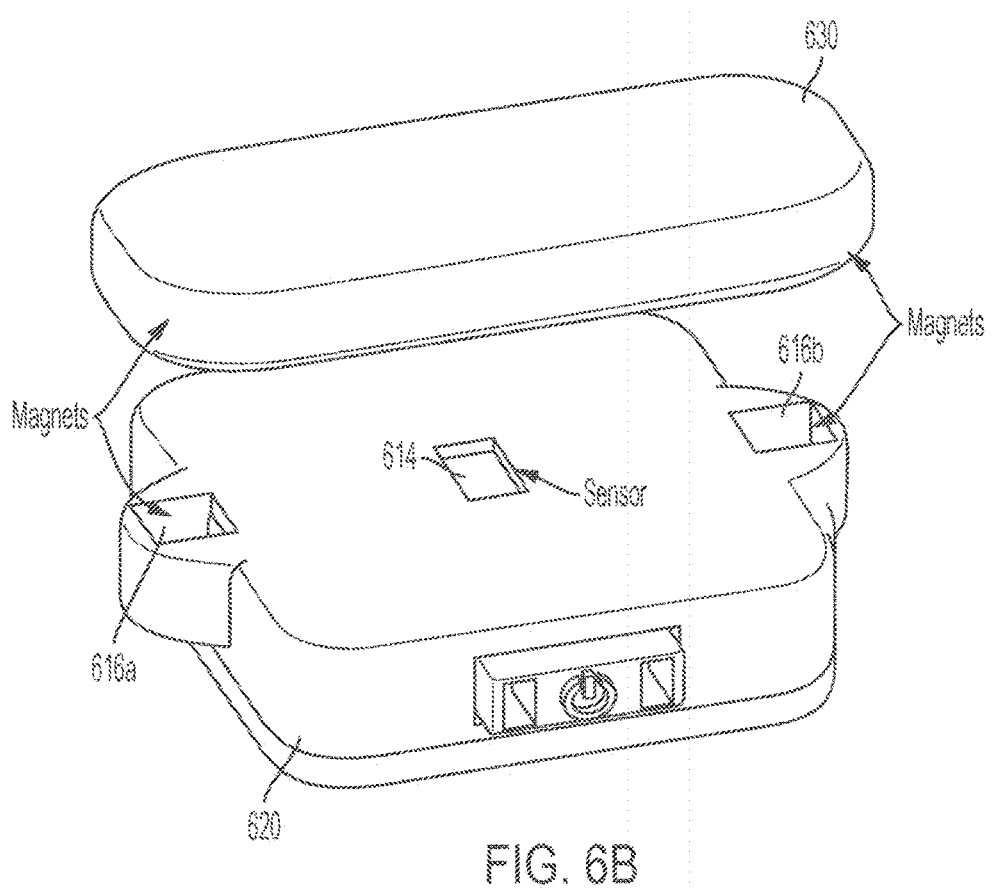
Figure 7:
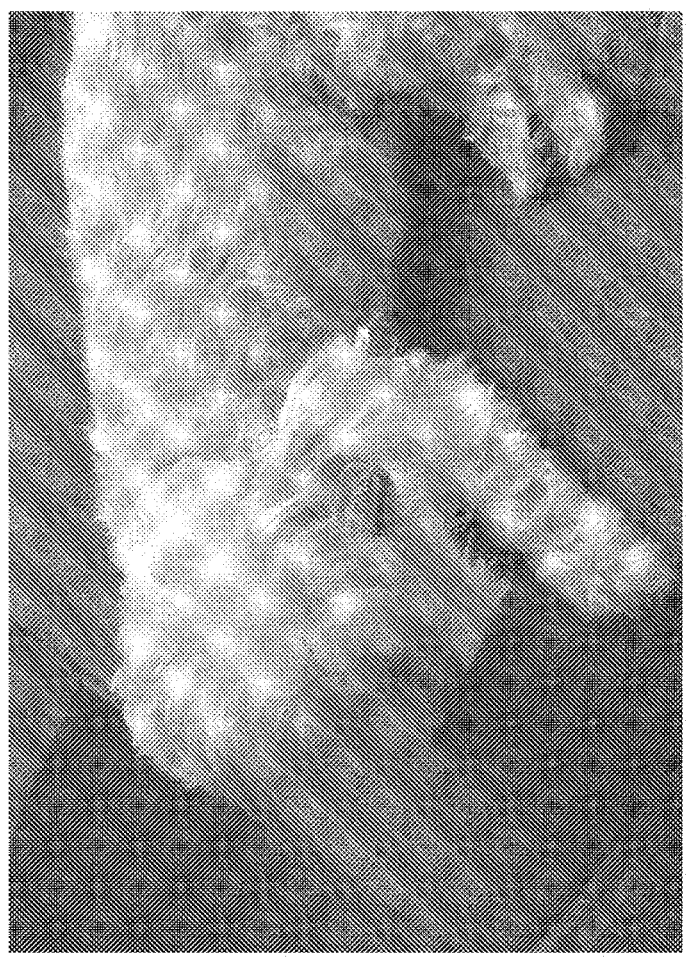
FIG. 7 illustrates the noninvasive vital signs measurement device of FIG. 6A when in use by an animal in accordance with some embodiments.

In some embodiments, system 600 includes a base portion 620 and a removable portion 630 coupled to the base portion via at least one fastener. Base portion 620 may include, for example, at least one sensor configured to sense one or more biological quantities from a wearer of the system 600 and associated circuitry configured to process and/or transmit the sensed biological signals from the system 600 to another device (e.g., a computing device with a display). FIG. 6B shows system 600 in which removable portion 630 has been separated from base portion 620 to expose sensor 614. Sensor 614 may be configured to sense one or more biological quantities (e.g., PPG measurements) from a user as discussed, for example, in connection with sensor 314 of system 300. Removable portion is reversibly coupled to base portion 620 using one or more fasteners. As shown in FIG. 6B, the one or more fasteners may include one or more magnets 616a and 616b configured to secure the removable portion 630 to the base portion 620 when a body part (e.g., an ear) is arranged between the base portion and the removable portion, as shown in FIG. 7. It should be appreciated that fasteners other than magnets may additionally or alternative be used to couple base portion 620 and removable portion 630 and embodiments are not limited in this respect. For instance, removable portion 630 may include a hinge on one side and a latch on the other side to enable removable portion 630 to be opened relative to base portion 620. Alternatively, one or more springs or other elastic member may be used on either end of removable portion 630 to enable the removable portion 630 to be separated from base portion 620 to expose sensor 614 and to enable a body part (e.g., an ear or finger) to be arranged above the sensor 614 between removable portion 630 and base portion 620. Accordingly, in some embodiments, removable portion 630 need not be completely removable from base portion 620, instead only be separable from base portion 620 to enable a body part to be arranged between the two portions of system 600.

The inventor has recognized and appreciated that one particularly useful application of a noninvasive vital signs measurement system (e.g., system 600) is to monitor vital signs for a non-human animal (e.g., a pet, livestock, etc.). FIG. 7 shows an example of use of system 600 to measure noninvasive vital signs of a cat by attaching system 600 to the cat's ear.

Conventional techniques for measuring non-human animal vital signs (e.g., heart rate, blood oxygenation) are invasive and typically require application of anesthesia to sedate the animal. For instance, such techniques often require technical skill (typically from a veterinarian) to place a catheter to make the measurements, expensive equipment that requires frequent maintenance and calibration, and an invasive procedure, which puts the animal at risk of infection at the catheter insertion site. By contrast, a noninvasive vital signs measurement system designed in accordance with the techniques described herein (e.g., system 600) is configured to obtain vital signs measurements without the use of anesthesia and is designed to easily and comfortably attach to an ear or other body part of an animal. Such a system may be coupled to the animal's ear without the need for specialized technical training thereby allowing for capturing one or more vital signs of the animal under normal conditions in the animal's natural environment.

Figure 8:
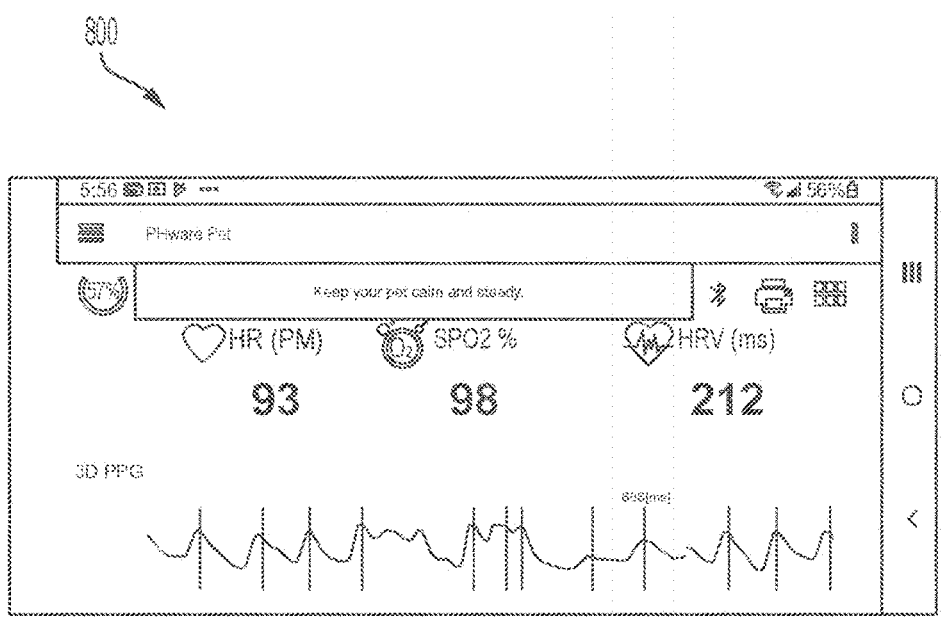
FIG. 8 illustrates a display configured to display vital signs measured using a noninvasive vital signs measurement device in accordance with some embodiments.

FIG. 8 shows an example of a display configured to communicate with a noninvasive vital signs measurement system (e.g., system 600) and to display measured vital signs from a non-human animal. For instance, display 800 may be included as part of a portable computing device (e.g., a smartphone). As shown, display 800 is configured to display a PPG waveform and one or more vital signs measurements determined based, at least in part, on the PPG measurements. For instance, display 800 may be configured to display heart rate information, oxygen saturation ($SpO_2$) information, and heart rate variability (HRV) information for a non-human animal to which the noninvasive vital signs measurement device is attached. It should be appreciated however, that not all embodiments require the display of multiple types of vital signs including, but not limited to the vital signs shown on the display of FIG. 8. For instance, some embodiments may only display a single vital signs measurement or no vital signs measurements at all. Rather, some embodiments may be configured to compare one or more measured vital signs to a threshold value or range and provide an indication when the vital signs measurement deviates from the threshold value and/or is outside of the range. Such an indication may alert a user of the measurement system or another user (e.g., a pet's owner) of the deviation. The provided indication may be a visual indication (e.g., as shown in FIG. 8), an audio indication, a tactile indication, or any combination thereof, as embodiments are not limited in this respect.

Figure 9:
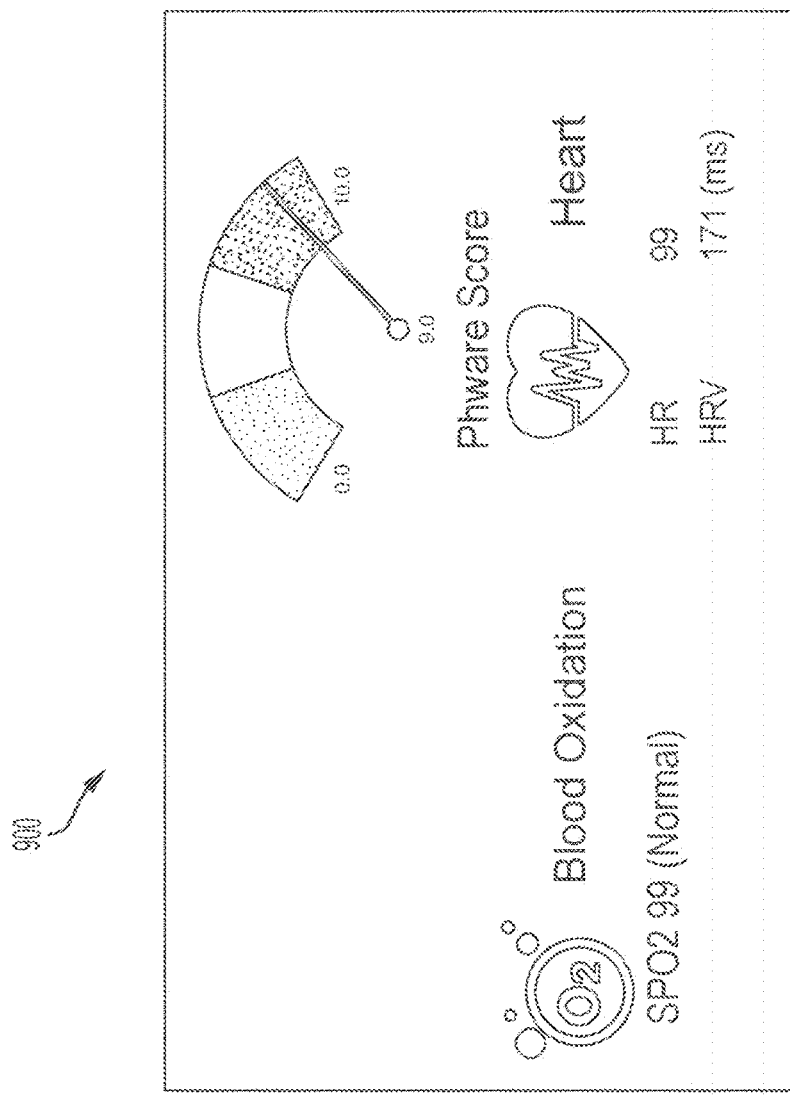
FIG. 9 illustrates an alternate display configured to display vital signs measured using a noninvasive vital signs measurement device in accordance with some embodiments.

In some embodiments, one or more vital signs measurements may be used to determine a single score associated with a wellness of a user. The vital signs measurements may be combined in any suitable way to determine the single score presented to the user or another user (e.g., a pet's owner). For instance, the single score may be a number between 0 and 10 and may be determined relative to references for similar animals as the animal being measured. In other embodiments, the single score may be a categorization (e.g., above average, normal, below average) with reference to similar animals. FIG. 9 illustrates a display 900 configured to display a plurality of vital signs and a single score (referred to herein as a Phware Score) determined based, at least in part, on the vital signs measured using a noninvasive vital signs measurement system, examples of which are described herein. Display 900 may be shown, for example, on a smartphone, laptop, tablet computer, swartwatch, or any other computing device configured to receive information from the noninvasive vital signs measurement system. In some embodiments, one or more of displays 500, 800, 900 (or other suitable displays may be configured as a touch screen display that enables a user to interact with the display via touch.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

The invention claimed is:

1. An apparatus for noninvasive measurement of vital signs from an ear of a non-human animal, said apparatus comprising:
a first portion having a first end and a second end and a second portion having a first end and a second end, the first portion and second portion couplable in multiple configurations relative to each other using at least one fastener, including a first configuration in which the first end of the first portion is adjacent the first end of the second portion and a second configuration in which the first end of the first portion is adjacent the second end of the second portion, the first and second portion couplable about the ear of the non-human animal to be arranged between the first portion and the second portion when coupled, the first portion including:
at least one light source configured to illuminate the ear of the non-human animal with light;
at least one sensor configured to sense light reflected from the ear of the non-human animal to determine a photoplethysmogram (PPG); and
at least one computer processor programmed to:
determine based, at least in part, on the PPG, a plurality of vital signs for the non-human animal, wherein the plurality of vital signs include heart rate, blood oxygen saturation, heart rate variability and respiration rate; and
output an indication of the plurality of vital signs.

2. The apparatus of claim 1, wherein the first portion includes a casing having a first side and a second side arranged opposite the first side, wherein the first side of the casing has a recessed portion formed therein, wherein the recessed portion includes the at least one sensor.

3. The apparatus of claim 2, wherein a surface area of the first side of the first portion is less than or equal to 1 inch by 1 inch.

4. The apparatus of claim 2, wherein the first side of the casing is formed of a flexible material.

5. The apparatus of claim 2, wherein the first side of the casing is contoured to facilitate positioning of the first side relative to the ear of the non-human animal.

6. The apparatus of claim 1, wherein the at least one fastener includes at least one magnet arranged on the first portion and/or the second portion.

7. The apparatus of claim 6, wherein the at least one magnet includes a plurality of magnets.

8. The apparatus of claim 1, wherein the at least one fastener is configured to enable the first portion to be completely removable from the second portion.

9. The apparatus of claim 1, wherein the at least one fastener is configured to secure the apparatus to the ear of the non-human animal.

10. The apparatus of claim 1, wherein a shape of the first portion and a shape of the second portion are different.

11. The apparatus of claim 1, wherein the at least one sensor is configured to continuously sense light reflected from the ear of the non-human animal to determine the PPG.

12. The apparatus of claim 1, further comprising:
a communications interface configured to communicate with a mobile computing device, wherein outputting an indication of the plurality of vital signs comprises sending the indication of the plurality of vital signs via the communications interface for display on the mobile computing device.

13. The apparatus of claim 1, wherein the at least one computer processor is further programmed to determine, based, at least in part, on the plurality of vital signs, a single score associated with a wellness of the non-human animal, and wherein outputting an indication of the plurality of vital signs comprises outputting the single score.

14. The apparatus of claim 13, wherein the single score is determined further based, at least in part, on reference information for a plurality of animals similar to the non-human animal from which the plurality of vital signs were determined.

15. The apparatus of claim 13, wherein the single score is a categorization determined with reference to a plurality of animals similar to the non-human animal from which the plurality of vital signs were determined.

* * * * *